United States Patent [19]

Rosencwaig et al.

[11] Patent Number: 4,750,822

[45] Date of Patent: Jun. 14, 1988

[54] METHOD AND APPARATUS FOR OPTICALLY DETECTING SURFACE STATES IN MATERIALS

[75] Inventors: Allan Rosencwaig, Danville; Jon Opsal; Walter L. Smith, both of Livermore, all of Calif.

[73] Assignee: Therma-Wave, Inc., Fremont, Calif.

[21] Appl. No.: 845,606

[22] Filed: Mar. 28, 1986

[51] Int. Cl.[4] ............................................. G01N 21/41
[52] U.S. Cl. ..................................... 356/445; 356/432
[58] Field of Search ................... 356/432, 432 T, 445, 356/446, 433; 374/5, 57

[56] References Cited

U.S. PATENT DOCUMENTS

| | | | |
|---|---|---|---|
| 4,243,327 | 1/1981 | Frosch et al. | 374/5 |
| 4,521,118 | 6/1985 | Rosencwaig | 356/376 |
| 4,522,510 | 6/1985 | Rosencwaig et al. | 374/5 |
| 4,579,463 | 4/1986 | Rosencwaig et al. | 356/432 |
| 4,632,561 | 12/1986 | Rosencwaig et al. | 374/5 |

OTHER PUBLICATIONS

Olmstead et al., "Temperature Dependence of the Si and Ge (111)2×1 Surface-State Optical Absorption", Physical Review B, vol. 33, No. 4, 15 Feb. 1986.

Sole et al., "Effect of Surface and Nonuniform Fields in Electroreflectance: Application to Ge", Physical Review B, vol. 17, No. 8, 15 Apr. 1978.

Heiland et al., "Surface Studies by Modulation Spectroscopy", Surface Science, 37 North-Holland Publishing Co.

Liu et al., "Picosecond Time-Resolved Plasma and Temperature-Induced Changes of Reflectivity and Transmission in Silicon", Appl. Phys. Lett 41(7), 1 Oct. 1982.

Primary Examiner—R. A. Rosenberger
Attorney, Agent, or Firm—Limbach, Limbach & Sutton

[57] ABSTRACT

A method and apparatus is disclosed for detecting defect surface states in any material and in particular semiconductors. In the subject device, a periodic localized excitation is generated at the surface of the sample with an intensity modulated pump laser beam. A probe laser beam is directed to the surface of the sample and changes in the probe beam which are in phase with the modulated pump frequency are detected. In the preferred embodiment, periodic changes in the optical reflectivity of the surface of the sample induced by an intensity modulated excitation beam are detected by measuring the corresponding modulations in the reflected power of the probe beam. Any time dependence of the probe beam modulated reflectance signal is monitored. An evaluation of defect surface states is then made by investigating the time dependence of the magnitude and/or phase of this probe beam modulated reflectance signal.

28 Claims, 2 Drawing Sheets

METHOD AND APPARATUS FOR OPTICALLY DETECTING SURFACE STATES IN MATERIALS

TECHNICAL FIELD

A new method is disclosed for evaluating surface states in a sample. The subject system is particularly suited for characterizing defect surface states.

BACKGROUND OF THE INVENTION

Every material has molecular and electronic energy states which characterize its composition. These energy states are typically defined in terms of the interior or bulk of the material. In the real world, all materials have surfaces with dangling atomic bonds which produce molecular and electronic energy states, called surface states, different than those present in the underlying bulk material.

The energy states at the surface of a sample are dependent upon the structure and the stoichiometry of the underlying material as well as on the actual physical and chemical conditions on the surface of the material. The portion of the surface states which is a function of the underlying material only is called the intrinsic surface states. The portion of the surface states which arises from other physical and chemical conditions on the sample surface is called the defect surface states. Typically, the defect surface states arise from surface contamination or from strucutral defects in the surface structure of the sample. The surface state of almost any sample will be affected to some degree by defect surface states in addition to the intrinsic surface states.

The importance of the existence of surface states is extremely significant in the semiconductor industry. As can be appreciated, it is desirable to manufacture samples that are as free from contaminants and surface defects as possible. Unfortunately, it is extremely easy to introduce such surface defects into a sample. For example, it has been shown that when silicon wafers are polished or etched, additional surface defect states are introduced. These defect states can adversely alter the performance of a semiconductor device. The subject invention is designed to provide a new and convenient means for detecting that portion of the surface states which are attributable to defect surface states. In this manner, contaminants and surface characteristics of a sample can be evaluated.

Considerable effort has been made in the past to develop methods for detecting and evaluating surface states. A very complete discussion of semiconductor surfaces as well as a number of methods for detecting these states can be found in the reference *Semiconductor Surfaces* by A. Many, North Holland Publishing Company, Amsterdam, 1971. As set forth in this reference, surface states can be evaluated by measuring the electric field effects at the surface. Techniques for measuring sample conductance and capacitance have been utilized. Surface states have also been measured through magnetic detection techniques. Most of these techniques are inadequate since they tend to be contact technologies and only yield information on intrinsic surface states.

Optical techniques have also been utilized. One technique, called a tunneling microscope, is described in "Real-Space Observation of pi-Bonded Chains and Surface Disorder on Si(111)2×1", Feenstra, et al., *American Physical Society*, Vol. 56, No. 6, Feb. 1986. Another technique, known as spectroscopic ellipsometry, requires the use of a polarized beam which is reflected off the surface of the sample. By measuring the change in angle of polarization of the reflected beam, some information can be derived regarding the surface states. A description of ellipsometry techniques can be found in the following articles by Aspnes, "Microstructural Information from Optical Properties in Semiconductor Technologies", and "Optical Detection and Minimization of Surface Overlayers on Semiconductors Using Spectroscopic Ellipsometry." Both of these articles are published in SPIE, Vol. 276, *Optical Characterization Techniques for Semiconductor Technology*, at pages 188 and 227 (1981). (See also "Anisotropies in the Above-Band-Gap Optical Spectra of Cubic Semiconductors," Aspnes, *The American Physical Society*, Vol. 54, No. 17, p. 1956, April 1985.)

Another tool for evaluating surface states is through a photoacoustic technique. The use of photoacoustic spectroscopy to study optical absorption of surface states is described in detail in *Photoacoustics and Photoacoustic Spectroscopy*, by Allan Rosencwaig, John Wiley & Sons, 1980. In a photoacoustic technique, an intensity modulated heating beam is directed to the surface of a sample. The absorption of the heating beam is then measured as the wavelength of the heating beam is varied. In the earliest experiments, the sample was sealed in a gas-filled cell. Absorption is monitored by detecting sonic vibrations in the gas with a microphone.

The latter technique is suitable for spectroscopic analysis of surface states on a relatively large spatial scale. More specifically, in order to get the wide wavelength range of the heating beam needed for spectroscopic analysis, it is necessary to use an incandescent light source which is modified by a monochrometer. The incandescent source cannot be focused to less than one millimeter in resolution.

In the technique described above, spectroscopic information is obtained about the combined intrinsic and defect surface states. In order to separate the intrinsic surface states from the defect surface states, further analysis is required. In this analysis, the change in phase of the output signal is monitored as the modulation or chopping frequency of the heating beam is varied. Unfortunately, this approach is very difficult to achieve in practice since the phase changes are extremely small.

Another spectroscopic technique is described in "Temperature Dependence of the Si and Ge(111) 2×1 Surface-State Optical Absorption," Olmstead and Amer, *American Physical Society*, Vol. 33, No. 4, page 2564, February 1986. In this case, periodic deviations of a probe beam reflected off the surface of the sample are studied to detect optical absorptions.

Electroreflectance and photoreflectance spectroscopy has also been used to evaluate surface states. In these techniques, the surface of a semiconductor is periodically excited either with an alternating electric field (electroreflectance) or an intensity modulated beam of light (photoreflectance). Changes in reflectivity in the sample due to this periodic excitation are then monitored. (See, for example, "Effect of Surface and Nonuniform Fields in Electroreflectance: Application to Ge," Del Sole and Aspnes, *Physical Review*, Vol. 17, No. 8, page 3310, April 1978, and "Surface Studies by Modulation Spectroscopy," Heiland and Monch, Surface Science, Vol. 37, page 30, 1973).

None of the above techniques combines all of the desired qualities of a practical analytical tool for the manufacturing environment. Therefore, it would be desirable to provide an alternate technique for detecting defect surface states which is quick, easy to operate, highly sensitive and has high spatial resolution capabilities.

Accordingly, it is the object of the subject invention to provide a new and improved method and apparatus for evaluating surface states.

It is another object of the subject invention to provide a new and improved method for isolating defect surface states from intrinsic surface states.

It is a further object of the subject invention to provide an apparatus for detecting defect surface states with micron scale spatial resolution.

It is still another object of the subject invention to provide an apparatus which will provide a semiconductor manufacturer with the ability to characterize the surface contamination and surface damage of silicon or gallium arsenide which might arise from various integrated circuit manufacturing processes.

SUMMARY OF THE INVENTION

In accordance with these and other objects, the subject invention provides for an optical measurement technique for evaluating surface states. The method and apparatus arises from the discovery that temporal changes in the signal arising from defect surface states can be induced when the sample is subjected to a relatively high energy modulated excitation source.

These changes were first observed when measurements were made of the periodic changes in the power of a probe beam reflected off a sample surface that was excited by a highly focused, intensity modulated pump beam. The measurement of periodic changes of the power of a probe beam reflected off a periodically excited sample is the subject of a group of prior publications. (See, "Detection of Thermal Waves Through Optical Reflectance," Rosencwaig, et al., *Applied Physics Letters*, Vol. 46, June 1, 1985; and "Ion Implant Monitoring with Thermal Wave Technology," Smith, et al., *Applied Physics Letters*, Vol. 47, September 1985. See also, U.S. Pat. application Ser. Nos. 612,075, 612,076, and 612,077, filed May 21, 1984, and U.S. application Ser. No. 707,485, filed Mar. 1, 1985, and incorporated herein by reference.)

All of the references cited above describe the evaluation of a sample by monitoring the power of a reflected probe beam. Spatial mapping of the sample can be made by tracking the beam over the surface of the sample.

It has now been discovered that if the pump and probe beams are held stationary at a focused point on the surface of the sample, the measured signal will change as a function of time. The signal will generally increase or decrease, as described in more detail below. In either case, the signal tends to change in a manner which is mathematically equivalent to a diffusion curve. Thus, the signal will initially show a rapid change and then become relatively flat. The time necessary for the diffusion-like effect to stabilize can be a few seconds to a few minutes.

It has been determined that the difference in signal between the initial measurement and the stabilized measurement represents the signal which is a function of the presence of defect surface states. One reason for this belief is that the signals measured after stabilization correspond quite closely to the signals measured for samples known to have very low concentrations of defect surface states. Also observed is the fact that the original signal will return after some period of time. Thus, if the sample is left undisturbed and then remeasured, the signal will once again return to its initial level, indicating that whatever processes tended to neutralize the defect surface states have been reversed.

The actual physical mechanism which causes the periodic reflectance signal to change over time is not fully understood. It has been postulated that contaminants, which may be responsible for the defect surface states, are driven away by the energy of the excitation beam through some type of diffusive process. Another possibility is that free charges that are generated in semiconductors by the excitation process diffuse from within the material to the surface and bind with the contaminants or surface defects to neutralize their effect on the surface states.

In the preferred embodiment of the subject invention, the changes in the modulated reflectance signal of the probe beam are monitored over time to evaluate the defect surface states in the sample. The apparatus utilized is identical to that described in the prior art references cited above, except that in this application, the time dependence of the signal is studied. Besides measuring the time dependent variations in the magnitude of the modulated reflectance signal of the probe beam, it is also possible to measure the time dependent variations in the phase of the modulated reflectance signal relative to the pump beam modulation frequency.

In addition to the modulated beam reflectance method, other highly focused and sensitive optical techniques may also be utilized to detect a time dependent signal from the defect surface states. For example, changes in the power of the transmittance of a probe beam through a sample or changes in optical scattering can be monitored. An apparatus for measuring optical transmittance and scattering is described in "Detection of Thermal Waves Through Modulated Optical Transmittance and Modulated Optical Scattering," Rosencwaig, et al., *Journal of Applied Physics*, Vol. 59, February 1986. (See also, U.S. Pat. application Ser. Nos. 728,759, filed Apr. 30, 1985, and 761,754, filed Aug. 1, 1985, and incorporated herein by reference.)

The above-outlined techniques all rely on the fact that the index of refraction at the surface of the sample will change periodically when it is periodically excited. These measurement techniques are very sensitive and produce a measurement which is a direct function of surface excitation.

It may also be possible to measure defect surface states using another optical technique developed by the applicants and covered in U.S. Pat. Nos. 4,521,118, issued June 4, 1985, and 4,522,510, issued June 11, 1985 and incorporated herein by reference. As described therein, the deviations of a probe beam reflected off the surface of the sample are measured. These deviations are the result of periodic changes of the local slope at the surface of the sample. In this type of measurement technique, the periodic changes in the local slope of the surface arise from a thermoelastic response and thus represent an average of the conditions existing at and below the surface. Accordingly, the component of the signal which is purely dependent on surface states is much smaller than in the reflectance type of techniques. Nonetheless, experiments have indicated that a changing temporal signal can still be detected. In certain materials and under certain circumstances, this technique may be a viable alternative.

The above references demonstrate that the detection of either periodic changes in the power of a probe beam or its periodic angular changes can be used to accurately measure surface characteristics in a sample. However, none of these prior references ever disclosed the significance of a localized, temporal variation in the modulated probe beam signal. More importantly, this time dependent variation was never utilized to characterize defect surface states in a sample.

Further objects and advantages of the subject invention will become apparent from the following detailed description taken in conjunction with the drawings in which:

DETAILED DESCRIPTION OF THE PREFERRED EMBODIMENT

Figure 1:
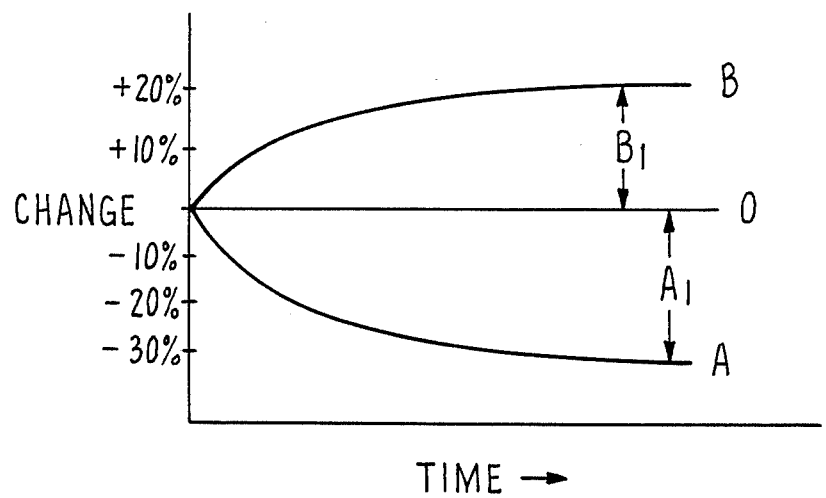
FIG. 1 is a graph illustrating the change in the magnitude of the modulated reflectance signal measured over time for two different samples.
Figure 2:
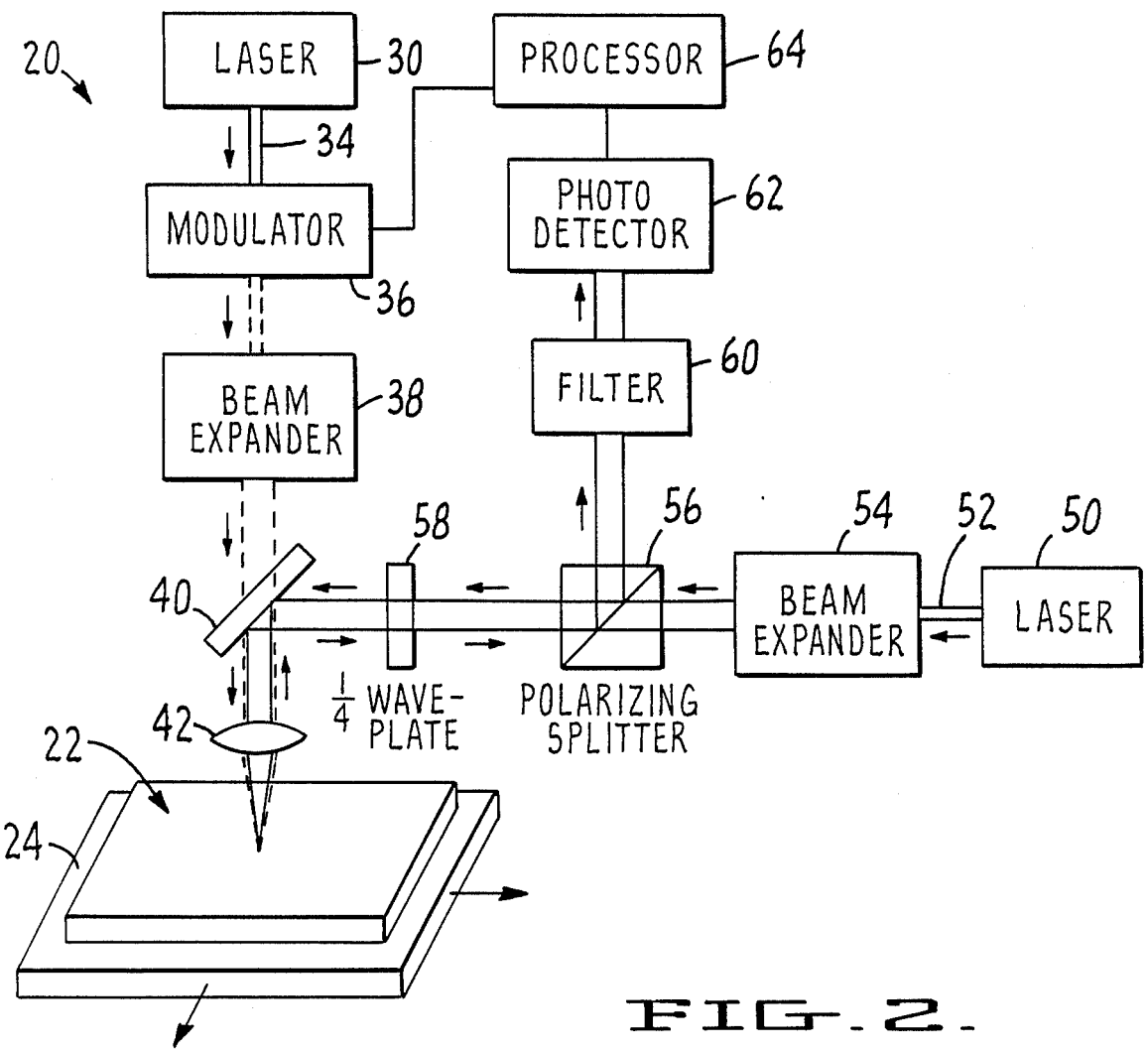
FIG. 2 is a schematic diagram illustrating the preferred arrangement for measuring variations in a probe beam over time and for carrying out the method of the subject invention.

In FIG. 1, a graph is provided illustrating two examples of the observed, time dependence of the excitation induced modulated reflectance signal generated by the device illustrated in FIG. 2. In this device, an intensity modulated excitation source is focused at the surface of the sample. This relatively powerful periodic excitation will induce periodic changes in the refractive index of the sample. The periodic changes can be monitored by directing a probe beam within the periodically excited region on the sample surface and monitoring the periodic changes in power of that reflected beam. The power of the probe beam varies periodically because periodic changes in the refractive index induce periodic changes in the optical reflectivity of the sample at the wavelength of the probe beam.

In the graph of FIG. 1, the horizontal axis illustrates elapsed time. The vertical axis is intended to illustrate the temporal variation in the magnitude of the excitation induced modulated reflectance signal defined in terms of a percentage. Thus, curve A represents a sample where the modulated reflectance signal decreases over time by roughly 30%. Curve B represents a sample where the signal rises by about 20%.

Both of these curves change monotonically over time in a manner that is apparently diffusion related. At time zero, the modulated reflectance signal apparently is a composite of both bulk and surface states. The surface state portion of the signal is further a function of both intrinsic surface states and defect surface states.

In the sample represented by curve A, the signal from the bulk states and surface states are all additive. As the modulated pump and probe beams continue to illuminate the microscopic spot on the sample surface, the defect surface states either diffuse away or become neutralized in a diffusion like process. As the signal from the defect surface state approaches zero, the net signal decreases until it reaches a level that is due solely to a combination of the bulk states and the intrinsic surface states. The time it takes for this to occur has been observed to range from a few seconds to a few minutes. In any case, the difference (shown as $A_1$) between the starting signal and the final signal represents a measure of the extent of defect surface states present at the start of the measurement.

The sample represented by curve B illustrates the situation where the defect surface states tend to produce a signal that is opposite in sign to the combination of the bulk and intrinsic surface states. As the signal from the defect surface states disappears, the net signal increases. Once again, the difference ($B_1$) between the initial signal and the end signal represents a measure of the level of defect surface states initially present.

By studying the temporal behavior of the modulated reflectance signal, defect surface states can be detected and characterized. More specifically, an evaluation can be made with regard to the time it takes the signal to reach some final value. Information can also be derived about the concentration of the defect surface states by studying the magnitude (i.e., $A_1$, $B_1$) of the change. Further information about the defect surface states can be obtained from a study of the temporal behavior of the phase of the modulated probe beam reflectance signal. Finally, information can be derived by observing whether the net signal increases or decreases which, in turn, indicates the charge state of the defect surface states.

It should be noted that for some samples tested, a signal which was initially observed to increase might then decrease or vice versa. It is postulated that in these samples, multiple defect surface states are present each with different charge state characteristics.

This measurement technique has proven to be highly sensitive. As noted above, the changes usually occur in only a few seconds or at most a few minutes. In practice, it is not necessary to wait until the signal has stabilized. More specifically, since the curves follow a diffusion profile, only a few data points are necessary to mathematically describe the remainder of the curve. Furthermore, the rate of change is fastest at the start of the measurement, such that the variation can be detected quickly. Thus, even if the diffusion process takes a few minutes, only a few seconds of measurement will be necessary to characterize localized areas of the sample.

The subject invention provides a unique method of evaluating and characterizing defect surface states by measuring the time dependence of the excitation induced modulation of the probe beam reflectance. As pointed out above, the presence of defect surface states in semiconductors is of great interest since these defect surface states can radically degrade the performance of an integrated circuit device.

Having described the basic theory and operation of the subject invention, a few specific devices for performing the method will be discussed. It should be pointed out that detailed descriptions of these devices are set forth in detail in applicant's prior patents and publications which have been incorporated herein by reference. The reader is therefore directed to these prior publications and patents for a discussion of the theory of operation behind the devices. The subject description will be limited herein to the specific components and the differences from the prior art devices.

Referring to FIG. 2, there is illustrated an apparatus 20 for carrying out the method of the subject invention. The apparatus 20 is designed to evaluate surface states in a sample 22. Sample 22 is shown resting on a stage 24. Stage 24 is capable of movement in two orthogonal directions in a manner such that the sample can be rastered with respect to the laser beams to facilitate mapping of the sample surface.

In accordance with the subject invention, an argon ion laser 30 is provided for exciting the surface of the sample. The argon laser 30 emits a 30 milliwatt pump beam 34 which is acousto-optically chopped with the modulator 36. The chopping frequency is on the order of 1-20 MHz. Intensity modulated pump beam 34 is then passed through both a beam expander 38 and a dichroic mirror 40 which is transparent to the argon beam. Beam 34 is focused to a one micron diameter spot on the sample surface with a lens 42. In the preferred embodiment, the power delivered to the localized spot is about 10 milliwatts. A similar periodic excitation can be provided by other sources such as a particle beam.

As described in applicants' prior applications U.S. application Ser. Nos. 612,076 and 707,485, cited above, the localized periodic excitation of the surface will give rise to periodic changes in the sample surface including periodic changes in the index of refraction. The changes in the index of refraction can be monitored by detecting the periodic reflectance changes at the sample surface through its interaction with a probe laser beam.

In the illustrated embodiment, a probe beam 52 is generated by a helium-neon laser 50. Beam 52 passes through an expander 54 as well as through a polarizing splitter 56. Polarizing splitter 56 is arranged to transmit the polarized coherent light emanating from laser 50. This splitter will also deflect all light whose polarization has been rotated 90° relative to the original polarization. As can be appreciated, by this arrangement, the specularly reflected returning probe beam 52 can then be directed upwards to photodetector 62 if the polarization of retroreflected probe beam 52 has been rotated by 90°.

Incident beam 52 is passed through a quarter wave plate 58 which functions to rotate the polarization of the probe beam by 45°. The beam is then deflected downwardly by dichroic mirror 40 which is transparent to the argon beam 34 but reflective for the probe beam 52. Beam 52 is passed through lens 42, coaxially with the modulated pump beam 34. As discussed in our prior applications, maximum signal strength for modulated reflectivity measurements can be made when both the pump and probe beams are focused to the same spot. In any event, the probe beam must be focused within the periodically excited region. The size of the periodically excited region is a function of the sample material, the chopping frequency of the pump beam, and the pump beam diameter.

Assuming that the surface of sample 22 is relatively smooth, beam 52 will be specularly reflected back up to mirror 40 where it will be redirected through quarter wave plate 58. Quarter wave plate 58 once again rotates the polarization of the beam 45°, such that it will be rotated a total of 90° from the incoming beam. In this orientation, the polarizing splitter will function to direct the beam upwardly.

Beam 52 is passed upwardly through a filter 60 which is designed to remove any traces of the modulated pump beam. Beam 52 is then directed onto the surface of photodetector 62. Photodetector 62 may be of any standard type which will emit a signal proportional to the total number of photons striking its surface.

Figure 3:
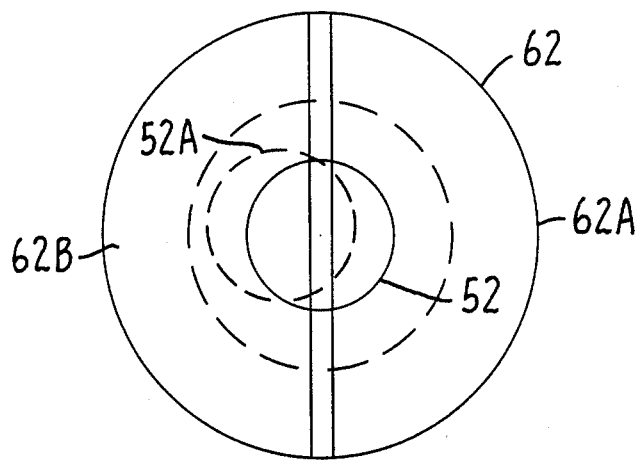
FIG. 3 is a schematic diagram of a split-cell detector of the type which may be used in the apparatus shown in FIG. 2 to give a measure of either the periodic deflection of the reflected probe beam induced by the periodic angular changes at the surface of the sample or the periodic changing power of a reflected probe beam.

It is important that the detector be arranged such that it be insensitive to any beam changes which are not the result of the changes in optical reflectivity of the surface. These conditions can be achieved by insuring that the probe beam substantially underfills the surface of the detector. This arrangement is best seen in FIG. 3 where photodetector 62 is shown capturing the beam 52. The particular photodetector 62 shown is a standard split cell detector which can also be used to monitor the displacement of the beam. The latter mode of operation will be discussed below. In this particular testing arrangement, the signals from both halves 62A and 62B of the photodetector are summed. In this manner, a signal proportional to the total number of photons in reflected beam 52 will be generated.

Two phantom beams 52A and 52B are drawn on the surface of the detector to illustrate the insensitivity to changes in beam diameter and position. Changes in beam diameter and position can occur due to changing thermal lens effects generated in the sample by the modulated pump source. Since the halves of the detector are summed, even if the beam 52A is deflected off center, the summed output of the detector will be the same. The output of the detector is also unchanged when the beam diameter varies since the areal density of the photons in the beam varies inversely with diameter. For example, if the diameter of the beam 52B is increased, its areal density will decrease and the total output of the detector will be the same. Therefore, the output of detector 62 is independent of changes in the beam diameter or position induced by thermal lens effects.

The signals from the detector are then supplied to processor 64. Processor 64 is phase locked with modulator 36 so that only periodic changes corresponding to the periodic excitation of the sample are evaluated. In this method, both the magnitude and the relative phase of the modulated reflectance signal can be measured.

All of the above elements are identical to the apparatus described in applicants' prior applications cited above. Thus, the output signals generated by photodetector 62 can be used by the processor to evaluate conditions at or near the surface of the sample. Such evaluation can include ion dopant monitoring or residue detection.

In accordance with the subject invention, defect surface states can be detected and characterized if the output signal is monitored by processor 64 as a function of time. The processor 64 is arranged to monitor the diffusion-like, temporal variations in either magnitude or relative phase of the high frequency modulated reflectance signal which occur when the pump and probe beams are held stationary at a localized point. It should be noted that the subject invention is not designed to give the exact stoichiometry of the surface states but rather can provide data which can be used to characterize the surface states. As noted above, with reference to FIG. 1, information regarding the time it takes for the signal to stabilize, the magnitude and phase of the change, and the sign of the defect surface states signal relative to the signal from the bulk and intrinsic surface states can be used to characterize the defect surface states of the sample.

Figure 4:
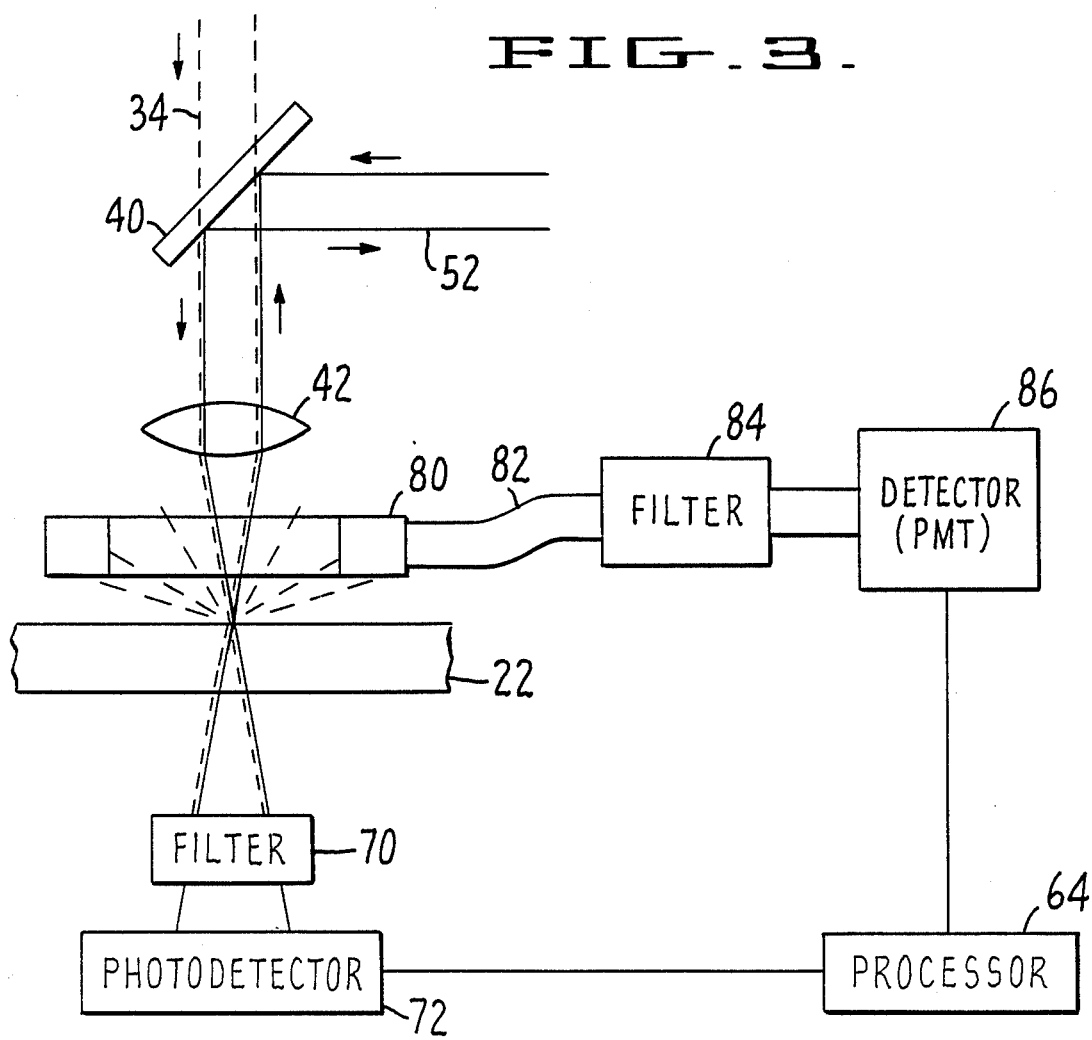
FIG. 4 is a partial schematic diagram of two alternate devices for measuring the periodic changes in the power of the probe beam and specifically illustrating the measurement of optical transmittance and optical scattering.

As pointed out above, applicant has developed other devices for detecting the periodic changes in optical refractive index of a sample surface. Two of these alternate expedients are illustrated in FIG. 4. These arrangements are described in greater detail in applicants' copending applications Nos. 728,759 and 761,754, cited above. In these devices, the periodic changes in optical refractive index of the sample are monitored through either optical transmittance or optical scattering detection techniques.

The illustration in FIG. 4 shows an apparatus where a modulated pump beam 34 is directed on the surface of a sample 22. The pump beam can be generated in the same manner as that shown in FIG. 2. Similarly, the generation and aiming of the probe beam 52 can also be the same. The beams 34 and 52 are focused by lens 42 onto the surface of the sample. In the case where the sample is at least partially transparent to the probe beam, its modulated changes in power can be detected after it passes through the sample. Beam 52 is first passed through a filter 70 for removing any of the radiation from pump beam 34. Photodetector 72 can be of any standard type as long as it is underfilled in the manner described above with reference to FIG. 3. In this manner, the signal will be independent of any changes in beam diameter or position. The output signal is then fed to processor 64 for evaluation as described above.

A signal which is proportional to the reflected power can also be measured through probe light scattered off the sample surface. In this instance, it is assumed that the captured portion of scattered light that is modulated at the pump beam frequency will vary periodically in proportion with the changes of optical reflectivity of the sample. A device for detecting scattered light is particularly suitable where the surface roughness or geometry of the sample makes it difficult to arrange the optical elements to accurately capture a specularly reflected beam. In this situation, an annular collector 80 is used to capture the scattered light. The scattered light is transferred along a fiber optic bundle through a filter 84 for removing any pump beam radiation. The beam is then captured with a detector which is preferably a photomultiplier tube 86. The signal is then transmitted to processor 64 for evaluation as discussed above.

Experimental data has shown that defect surface states can also be detected by monitoring the time dependence of the periodic deflection of the probe beam induced by periodic angular changes at the surface of the sample. As noted above, for the samples tested, this technique appears to be less sensitive than the modulated reflectance monitoring technique. However, usable results can be obtained and it is intended that the scope of the subject invention include this type of measurement technique.

The measurement of the deflection of a probe beam off the surface of the sample is described in detail in applicants' U.S. Pat. Nos. 4,521,118 and 4,522,510, cited above.

This measurement can be made with the device illustrated in FIG. 2. Specifically, the sample surface is periodically excited as described above. A probe beam 52 from laser 50 is then focused onto the surface of the sample. Unlike the modulated reflectance measurements, maximum signal strength for the periodic deflection signal is generally obtained when the probe beam is spaced from the pump beam a distance of one to two microns. At this location, the angular surface changes in the sample are the greatest. The beam is then redirected up to the photodetector in the manner described above with FIG. 2. Changes in the position of the beam due to the periodic angular changes at the surface of the sample can be detected using a split detector shown in FIG. 3. In this case, rather than adding the signals from segments 62A and 62B, the signals are subtracted. As the angle of deflection of the beam increases, the difference in the output signals of the two segments 62A, 62B will increase. In addition, because the signal is subtracted, any changes in the beam diameter or changes in power due to changes in reflectance, are canceled. The output signals are then evaluated by the processor over time in the manner described above.

In summary, there has been provided a new and improved method for detecting and characterizing defect surface states. In accordance with the subject method, the sample surface is periodically excited with an intensity modulated laser beam. A probe beam is then directed to the periodically excited region and interacts with the sample surface. Periodic changes of the probe beam are then detected and any variation in the changes, over time, are monitored. By monitoring the variations over time of the modulated probe beam signal, defect surface states can be detected and characterized.

While the subject invention has been described with reference to preferred embodiments, it is to be understood that various changes and modifications could be made therein, by one skilled in the art, without varying from the scope and spirit of the subject invention as defined by the appended claims.

We claim:

1. A method of obtaining information useful for evaluating surface states in a sample comprising the steps of:
   a. generating a localized periodic excitation at the surface of the sample;
   b. directing a probe beam of radiation within the periodically excited region of the sample;
   c. thereafter, detecting periodic changes in the probe beam that are synchronous with the periodic excitation and generating a signal corresponding thereto; and
   d. monitoring the variation in said signal as a function of time to provide information which can be used to evaluate the defect surface states of the sample.

2. A method as recited in claim 1 wherein the variation over time of the magnitude of the signal is monitored.

3. A method as recited in claim 1 wherein the variation over time of the relative phase of the signal with respect to the phase of the periodic excitation is monitored.

4. A method as recited in claim 1 wherein the rate of variation over time of the signal is monitored.

5. A method as recited in claim 1 wherein the direction of variation over time of the signal is monitored.

6. A method as recited in claim 1 wherein the periodic changes that are detected in step c are changes in the power of the probe beam.

7. A method as recited in claim 6 wherein changes in the power of a specularly reflected probe beam are monitored.

8. A method as recited in claim 6 wherein the proportional changes in the power in a diffusely scattered probe beam are monitored.

9. A method as recited in claim 6 wherein the changes in the transmittance of the probe beam are monitored.

10. A method as recited in claim 1 wherein the changes detected in the probe beam in step c are periodic changes in the position of the probe beam induced by periodic angular changes at the sample surface.

11. A method as recited in claim 1 wherein said step of generating a localized periodic excitation is performed by focusing an intensity modulated pump beam from a laser at a localized spot at the surface of the sample.

12. A method as recited in claim 11 wherein the probe beam is directed coaxially with the intensity modulated pump beam and the periodic changes in the power of the probe beam are detected.

13. An apparatus for obtaining information useful for evaluating surface states in a sample comprising:

means for inducing a periodic, localized excitation at the surface of the sample;

probe means for emitting a beam of radiation;

means for directing the beam from the probe means within the periodically excited region on the sample surface;

means for detecting the periodic changes in the probe beam after it has interacted with the sample;

means for processing the detected changes that are synchronous with the periodic excitation and generating a signal corresponding thereto; and means for monitoring the variation of said signal as a function of time to provide information which can be used to evaluate the defect surface states of the sample.

14. An apparatus as recited in claim 13 wherein said monitor means monitors the variation of the magnitude of the signal over time.

15. An apparatus as recited in claim 13 wherein said monitor means monitors the variation over time of the relative phase of the signal with respect to the phase of the periodic excitation.

16. An apparatus as recited in claim 13 wherein said monitor means monitors the rate of variation over time of the signal.

17. An apparatus as recited in claim 13 wherein said monitor means monitors the direction of the variation of the signal over time.

18. An apparatus as recited in claim 13 wherein said means for detecting the periodic changes in the probe beam functions to detect the periodic changes in power of the probe beam.

19. An apparatus as recited in claim 18 wherein the periodic changes in power are detected from a specularly reflected probe beam.

20. An apparatus as recited in claim 18 wherein said detecting means measures the proportional changes in the power of a diffusely scattered probe beam.

21. An apparatus as recited in claim 18 wherein the detecting means measures a transmittance of the probe beam.

22. An apparatus as recited in claim 13 wherein said means for inducing a periodic localized heating at the surface of the sample is provided by an intensity modulated beam from a pump laser source.

23. An apparatus as recited in claim 22 wherein said probe beam is directed coaxially with the beam from the pump laser source.

24. An apparatus for obtaining information useful for evaluating surface states in a sample comprising:

a pump laser for emitting a beam of radiation;

means for intensity modulating the pump beam;

probe means for emitting a beam of radiation;

means for focusing the intensity modulated pump beam and the probe beam to a localized spot on the surface of the sample such that the pump beam periodically excites the sample surface and the probe beam is specularly reflected;

means for detecting the periodic changes in the power of the reflected probe beam;

means for processing the detected changes in the power of the probe beam that are synchronous with the frequency of the modulating means and generating a signal corresponding thereto; and means for monitoring the variation of said signal as a function of time to provide information which can be used to evaluate the defect surface states of the sample.

25. An apparatus as recited in claim 24 wherein said monitor means monitors the variation of the magnitude of the signal over time.

26. An apparatus as recited in claim 24 wherein said monitor means monitors the variation over time of the relative phase of the signal with respect to the phase of the modulating means.

27. An apparatus as recited in claim 24 wherein said monitor means monitors the rate of variation over time of the signal.

28. An apparatus as recited in claim 24 wherein said monitor means monitors the direction of the variation of the signal over time.

* * * * *